US005145951A

United States Patent [19]

Voges et al.

[11] Patent Number: 5,145,951

[45] Date of Patent: Sep. 8, 1992

[54] PEPTIDES RETROVIRAL PROTEASE INHIBITORS COMPRISING 2-AMINO-2-METHYLPROPIONIC ACID

[76] Inventors: Klaus-Peter Voges; Dieter Häbich; Jutta Hansen; Arnold Paessens, all c/o Bayer Aktiengesellschaft, D 5090 Leverkusen, Bayerwerk, Fed. Rep. of Germany

[21] Appl. No.: 639,627

[22] Filed: Jan. 10, 1991

[30] Foreign Application Priority Data

Jan. 18, 1990 [DE] Fed. Rep. of Germany ....... 4001236

[51] Int. Cl.[5] .......................... C07K 5/04; C07K 5/06; A61K 37/64; A61K 37/02

[52] U.S. Cl. .................................... 530/330; 530/331

[58] Field of Search ..................... 514/18, 19; 530/330, 530/331; 562/561, 575

[56] References Cited

FOREIGN PATENT DOCUMENTS

| | | |
|---|---|---|
| 184550 | 6/1986 | European Pat. Off. . |
| 337714 | 10/1989 | European Pat. Off. . |
| 0357332 | 3/1990 | European Pat. Off. . |
| 0374097 | 6/1990 | European Pat. Off. . |
| 2203740 | 10/1988 | United Kingdom . |

OTHER PUBLICATIONS

Methods In Enzymology, vol. XXXIV, "Affinity Techniques, Enzyme Purification: Part B", Bovine Trypsin and Thrombin, Hixson, Jr. and A. H. Nishikawa, pp. 440–448, Academic Press, 1974.

Methods In Enzymology, vol. XXXIV, "Affinity Techniques, Enzyme Purification: Part B", Chymotrypsin(s), Tomlinson and Viswanatha, pp. 415–420, Academic Press 1974.

Affinity Chromatography, Biospecific Sorption; Affinity Chromatography of Chymotrypsin on Soybean Trypsin Inhibitor Sepharose: Applications in Genetics and Nuclide Labelling, Gabel, Kasche, Amneus and Lundqvist, pp. 99–102, Pergamon Press, 1977.

Applied Microbiology and Biotechnolgoy, Springer-Verlag 1979, Biotechnol. 6.; p. 195 (1979); "Recovery of Free Enzymes from Product Liquors by Bio-Affinity Adsorption: Trypsin Binding by Immobilised Soybean Inhibitor", Halling and Dunnill.

The Journal of Biological Chemistry, vol. 255, No. 15, Aug. 10, 1980 p. 7089, "Human Red Cell Purine Nucleoside Phosphorylase, Purification By Biospecific Affinity Chromatography and Physical Properties", Osborne, Mar. 17, 1980.

Hoppe-Scyler's Z. Physiol. Chem., vol. 361, p. 543, Apr. 1980, "Purification of Human and Bovine Alkaline Phosphatases by Affinity Chromatography", Mossner, Boll and Pfleiderer.

Analytical Biochemistry, vol. 107, p. 341, (1980), "Affinity Chromatographic Sorting of Carboxypeptidase A and its Chemically Modified Derivatives", Cueni, Bazzone, Riordan & Vallee, Mar. 31, 1980.

Hoppe-Seyler's Z. Physiol. Chem., vol. 359, p. 1019, Aug. 1978, "Affinity Chromatography of Bovine Bran β-Hexosaminidases with Substrate as Affinity Ligand", Lisman and Overdijk, May 1978.

Biochem. J. (1978), vol. 175, p. 125, "Purification of the Hexokinases by Affinity Chromatography on Sepharose-N-Aminoacylglucosamine Derivatives", Wright, Warsy, Holroyde and Trayer, Feb. 1978.

Archives of Biochemistry and Biophysics, vol. 198, No. 2, Dec. 1979, p. 533, "Quantitative Affinity Chromatography of α-Chymotrypsin", Dunn and Gilbert, Aug. 10, 1979.

T. J. McQuade et al., *Science* 247:454–456, 26 Jan. 1990.

A. G. Tomasselli et al., *Biochemistry* 29: 264–269, 1990.

*Primary Examiner*—Robert A. Wax

*Assistant Examiner*—Stephen Walsh

[57] ABSTRACT

Antiviral peptides of the formula

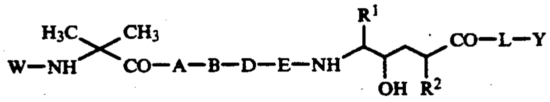

in which

W is an amino protecting group,

A,B,D,E and L each independently is a direct bond, or a radical of the formula

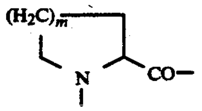 or

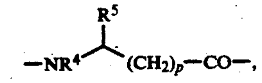

$R^1$ and $R^2$ each independently is cycloakyl or optionally substituted alkyl or alkenyl, Y is $-NHR^{10}$, and $R^{10}$ is cycloalkyl or optionally substituted alkyl, and their physiologically acceptable salts.

The formula includes a 2-amino-2-methylpropionic acid (AiB) residue, which may optionally be protected, as the N-terminal α-amino acid. The peptides are expected to be useful as medicaments, in particular as antiviral agents in human and veterinary medicine. The peptides are shown to inhibit aspartyl proteases including human immunodeficiency virus (HIV) protease, to have anti-HIV activity and to inhibit the proliferation of HIV in HIV-I infected human lymphocytes. The peptides are expected to be useful in treating patients having HIV related disorders such as ARC and AIDS.

8 Claims, No Drawings

PEPTIDES RETROVIRAL PROTEASE INHIBITORS COMPRISING 2-AMINO-2-METHYLPROPIONIC ACID

The invention relates to new peptides, to a process for their preparation and to their use as medicaments, in particular as antiviral agents in human and veterinary medicine.

GB-A 2,203,740 and EP 337,714 described peptides which have antiviral activity against the "human immunodeficiency virus" (HIV).

In addition, EP-A2 184,550 describes renin-inhibitory peptides in which 2-amino-2-methylpropionic acid (AIB) is linked to an adjacent amino acid group via an oxygen bridge.

The present invention relates to new peptides of the general formula (I)

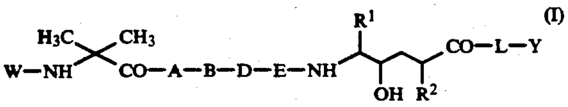

(I)

in which

W represents an amino protecting group, or represents a group of the formula

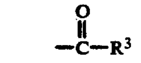

in which $R^3$ denotes hydrogen, straight-chain or branched alkyl having up to 8 carbon atoms or aryl having 6 to 10 carbon atoms, which may in turn be substituted by halogen, hydroxyl, nitro, trifluoromethyl or by straight-chain or branched alkyl or alkoxy having up to 8 carbon atoms, A, B, D, E and L are identical or different and represent a direct bond or represent a radical of the formula

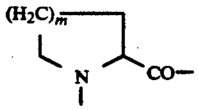

in which m denotes the number 1 or 2, or represent a group of the formula

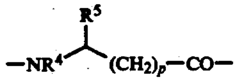

in which p denotes the number 0, 1 or 2, $R^4$ denotes hydrogen, straight-chain or branched alkyl having up to 8 carbon atoms, or phenyl, $R^5$ denotes cycloalkyl having 3 to 8 carbon atoms or aryl having 6 to 10 carbon atoms, or denotes hydrogen or straight-chain or branched alkyl having up to 8 carbon atoms, which is optionally substituted by cycloalkyl having 3 to 8 carbon atoms or by aryl having 6 to 10 carbon atoms, which in turn is substituted by hydroxy, halogen, nitro, alkoxy having up to 8 carbon atoms or by the group $-NR^6R^7$, or which is optionally substituted by a 5- or 6-membered nitrogen-containing heterocycle or indolyl, in which the corresponding —NH functions are optionally protected by alkyl having up to 6 carbon atoms or by an amino protecting group, or which is optionally substituted by alkylthio having up to 6 carbon atoms, hydroxyl, mercapto, guanidyl or by a group of the formula $-NR^6R^7$ or $R^8-OC-$, in which $R^5$ and $R^7$ are identical or different and denote hydrogen, straight-chain or branched alkyl having up to 8 carbon atoms or phenyl and $R^8$-denotes hydroxyl, benzyloxy, alkyloxy having up to 6 carbon atoms or the abovementioned $-NR^5R^7$ group, in their D- or L-form, or as a D,L-isomer mixture, preferably in the L-form, $R^1$ and $R^2$ are identical or different and represent cycloalkyl having 3 to 8 carbon atoms, represent straight-chain or branched alkyl or alkenyl having up to 10 carbon atoms, which is optionally substituted by cycloalkyl having 3 to 8 carbon atoms or aryl having 6 to 10 carbon atoms, which may in turn be monosubstituted to trisubstituted by identical or different substituents from the series comprising halogen, cyano and nitro or by a group of the formula $-OR^9$, in which $R^9$ denotes hydrogen or a typical hydroxyl protecting group, Y represents a group of the formula $-NHR^{10}$, in which $R^{10}$ denotes cycloalkyl having 3 to 8 carbon atoms, or denotes straight-chain or branched alkyl having up to 8 carbon atoms, which is optionally substituted by pyridyl or phenyl, and their physiologically acceptable salts.

Amino protecting groups in the context of the invention are the amino protecting groups customarily used in peptide chemistry.

These preferable include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrogenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, 2-nitrobenzyloxycarbonyl, 3,4,5-trimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, cyclohexoxycarbonyl, 1,1-dimethylethoxycarbonyl, adamantylcarbonyl, phthaloyl, 2,2,2-trichloroethoxycarbonyl, 2,2,2-trichloro-tert-butoxycarbonyl, methyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene.

Hydroxyl protecting groups in the context of the invention are, for example, trimethylsilyl, triethylsilyl, triisopropylsilyl, tert-butyl-dimethylsilyl, tert.butyl-diphenylsilyl, 2-nitrobenzyl, trifluoromethoxy, benzyl (Bzl), tert.-butyl ($^t$Bu), 2,2,2-trichloroethyl (Tre), 4-picolyl ether (Pic), acetyl (Ac) or 4-toluenesulphonyl.

The compounds of the general formula (I) according to the invention have several asymmetric carbon atoms. They may be present independently of one another in the D- or L-form. The invention includes the optical antipodes as well as the isomer mixtures or racemates. Preferably, the groups A, B, D, L and M are present independently of one another in the optically pure form, preferably in the L- form.

The general formula Xa

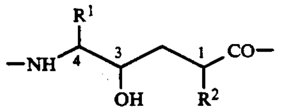
(Xa)

has 3 asymmetric carbon atoms (1, 3 and 4) which may be present independently of one another in the R- or S-configuration. Preferably, this group is present in the 1R, 3S, 4S-configuration, 1R, 3R, 4S-configuration, 1S, 3R, 4S-configuration or in the 1S, 3S, 4S-configuration. The 1S, 3S, 4S-configuration is particularly preferred.

The compounds of the general formula (I) according to the invention may be present in the form of their salts. These may be salts with inorganic or organic acids or bases. The acid addition products preferably include salts with hydrochloric acid, hydrobromic acid, hydriodic acid, sulphuric acid, phosphoric acid or with carboxylic acids such as acetic acid, propionic acid, oxalic acid, glycolic acid, succinic acid, maleic acid, hydroxymaleic acid, methylmaleic acid, fumaric acid, adipic acid, malic acid, tartaric acid, citric acid, benzoic acid, cinnamic acid, lactic acid, ascorbic acid, salicylic acid, 2-acetoxybenzoic acid, nicotinic acid, isonicotinic acid, or sulphonic acids such as methanesulphonic acid, ethanesulphonic acid, benzenesulphonic acid, toluenesulphonic acid, naphthalene-2-sulphonic acid or naphthalenedisulphonic acid.

Preferred compounds of the general formula (I) are those in which

W represents one of the abovementioned amino protecting groups, preferably tert.butyloxycarbonyl (Boc), 9-fluorenylmethyloxycarbonyl (Fmoc) or benzyloxycarbonyl (Z), or represents a group of the formula

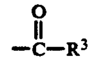

in which $R^3$ denotes hydrogen, straight-chain or branched alkyl having up to 6 carbon atoms or phenyl, which may in turn be substituted by fluorine, chlorine, bromine or by straight-chain or branched alkyl or alkoxy having up to 6 carbon atoms, A, B, D, E and L are identical or different and represent a direct bond or represent proline, or represent a group of the formula

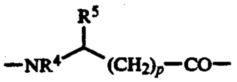

in which

P denotes the number 0 or 1, $R^4$ denotes hydrogen or straight-chain or branched alkyl having up to 6 carbon atoms, or phenyl, $R^5$ denotes cyclopentyl or cyclohexyl, or hydrogen, or phenyl, or straight-chain or branched alkyl having up to 6 carbon atoms, which may optionally be substituted by hydroxyl, HO—CO— or $H_2N$—CO—, or is substituted by cyclohexyl or naphthyl or phenyl, each of which may in turn be substituted by fluorine, chlorine, nitro or alkoxy having up to 6 carbon atoms, or is substituted by indolyl, imidazolyl, pyridyl, triazolyl or pyrazolyl, where the corresponding —NH functions are optionally protected by alkyl having up to 4 carbon atoms or by an amino protecting group, in their D- or L-form, or as a D,L-isomer mixture, preferably in the L-form, $R^1$ and $R^2$ are identical or different and represent cyclopropyl, cyclopentyl or cyclohexyl, represent straight-chain or branched alkyl or alkenyl having up to 8 carbon atoms, which are optionally substituted by cyclopropyl, cyclobutyl, cyclopentyl, cyclohexyl, cycloheptyl or phenyl, which is in turn monosubstituted or disubstituted by identical or different substituents from the series comprising fluorine, chlorine, bromine, cyano and nitro or by a group of the formula $—OR^9$, in which $R^9$ denotes hydrogen, tert.butyl or benzyl, Y represents a group of the formula $—NHR^{10}$, in which $R^{10}$ denotes straight-chain or branched alkyl having up to 6 carbon atoms, which is optionally substituted by cyclopropyl, cyclopentyl, cyclohexyl, phenyl or pyridyl, and their physiologically acceptable salts.

Particularly preferred compounds of the general formula (I) are those in which

W represents the amino protecting groups Boc, Fmoc or benzyloxycarbonyl, or represents a group of the formula

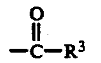

in which $R^3$ denotes hydrogen, straight-chain or branched alkyl having up to 4 carbon atoms or phenyl, A, B, D, E and L are identical or different and represent a direct bond or represent proline or represent a group of the formula

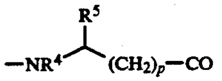

in which p denotes the number 0 or 1, $R^4$ denotes hydrogen or methyl, $R^5$ denotes cyclopentyl or straight-chain or branched alkyl having up to 4 carbon atoms, which is optionally substituted by hydroxyl, HO—CO— or $H_2N$—CO—, or is substituted by cyclohexyl or naphthyl or phenyl, each of which may in turn be substituted by fluorine, chlorine, or alkoxy having up to 4 carbon atoms, or is substituted by imidazolyl, triazolyl, pyridyl or pyrazolyl, where the NH function is optionally protected by methyl, benzyloxymethylene or t-butyloxycarbonyl (Boc), in their D- or L-form, or as a D,L-isomer mixture, preferably in the L-form, $R^1$ and $R^2$ are identical or different and represent cyclopropyl, cyclopentyl or cyclohexyl, or represent straight-chain or branched alkyl or alkenyl having up to 6 carbon atoms, which are optionally substituted by cyclopropyl, cyclopentyl, cyclohexyl, or phenyl which in turn is substituted by a group of the formula —$OR^9$, in which $R^9$ denotes hydrogen, tert.butyl or benzyl, Y represents a group of the formula —$NHR^{10}$, in which $R^{10}$ denotes straight-chain or branched alkyl having up to 4 carbon atoms, which is optionally substituted by cyclopropyl, cyclohexyl, phenyl or pyridyl, and their physiologically acceptable salts.

In addition, a process for the preparation of the compounds of the general formula (I) has been found, characterized in that compounds of the general formula (II)

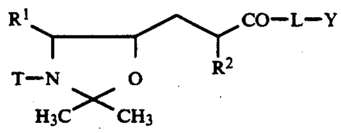

(II)

in which $R^1$, $R^2$, L and Y have the abovementioned meanings and

T represents one of the abovementioned amino protecting groups, preferably benzyloxycarbonyl, are reduced with ring opening in inert solvents to give the aminoalcohols of the formula (III)

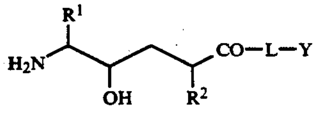

(III)

in which $R^1$, $R^2$, L and Y have the abovementioned meanings, and subsequently condensed by a customary method with compounds of the formula (IV)

T'—E'—OH (IV)

in which

T' has the abovementioned meaning of T and is identical to or different from this and E' has the abovementioned meaning of E, but does not represent a direct bond, and in a next step, either the protecting group T' is first removed, the compounds are deblocked again and reacted with compounds of the general formula (V)

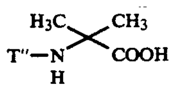

(V)

in which

T'' has the abovementioned meaning of T and is identical to or different from this, if appropriate with activation of the carboxylic acid by a customary method, to give compounds of the general formula (Ia)

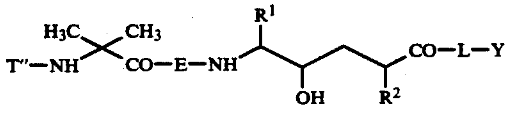

(Ia)

in which T'', E, $R^1$, $R^2$, L and Y have the abovementioned meanings, or the amino acid groups B and D are first introduced in analogy to the above-described reaction with the compounds of the formula (IV) with activation and deblocking and reacted in a last step with compounds of the general formula (VI)

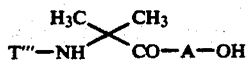

(VI)

in which

A has the abovementioned meaning and

T''' has the abovementioned meaning of T and is identical to or different from this.

The process according to the invention can be illustrated by way of example by means of the following equations:

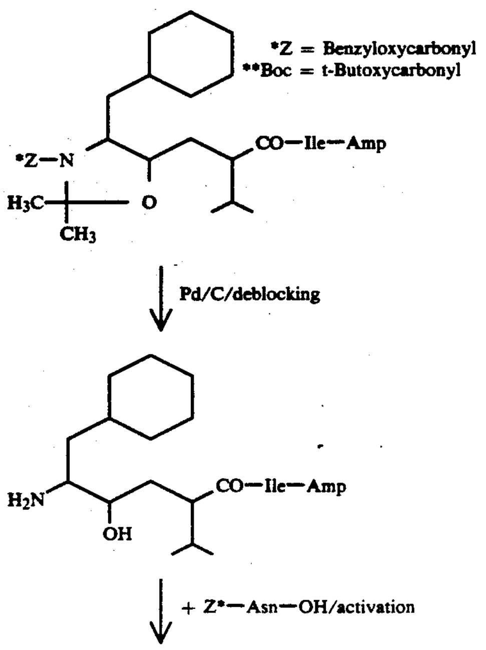

-continued
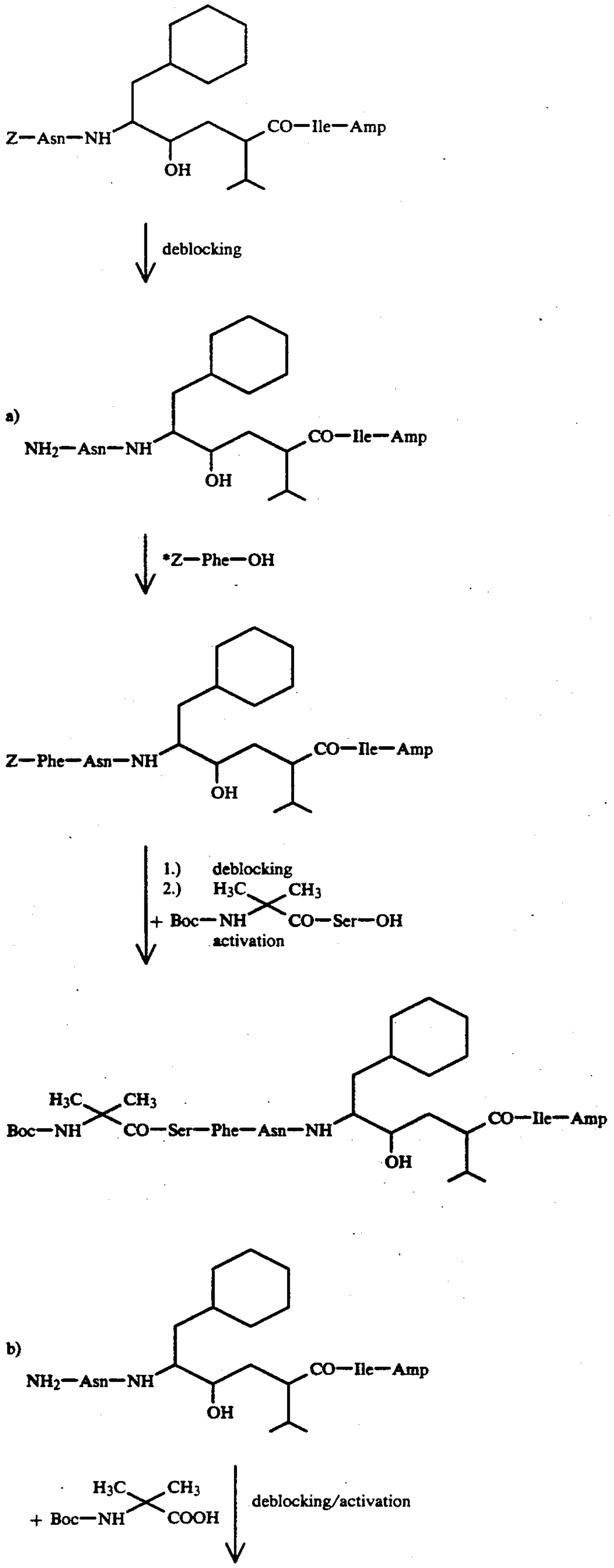

-continued

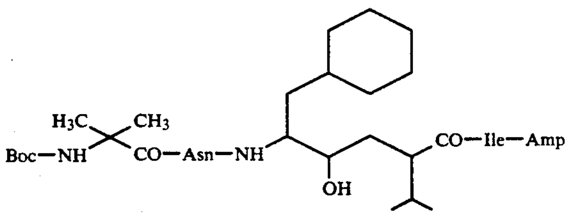

Suitable solvents for all process steps are the customary inert solvents which do not change under the reaction conditions. These preferably include organic solvents such as ethers, for example diethyl ether, glycol mono- or dimethyl ether, dioxane or tetrahydrofuran, or hydrocarbons such as benzene, toluene, xylene, cyclohexane or mineral oil fractions or halogenohydrocarbons such as methylene chloride, chloroform, carbon tetrachloride, or dimethyl sulphoxide, dimethyl formamide, hexamethylphosphoramide, ethyl acetate, pyridine, acetonitrile, triethylamine or picolines. It is also possible to use mixtures of the solvents mentioned.

Methanol and ethyl acetate are particularly preferred for the reduction.

The reduction of the compounds of the general formula (II) is carried out either using the customary catalysts, such as, for example, palladium hydroxide or palladium/carbon, preferably using palladium/carbon or by means of a catalytic transfer hydrogenation in a manner known per se [compare Tetrahedron 41, 3469 (1985), 3463 (1985), Synthesis 1987, 53].

The catalyst is added in an amount from 0.01 to 0.5 mol, preferably from 0.02 to 0.05 mol, relative to 1 mol of the compound of the general formula (II).

The reduction is carried out in a temperature range from 40° C. to 160° C., preferably from 80° C. to 100° C.

The reduction can be carried out both at normal pressure and at elevated or reduced pressure (for example 0.5 to 5 bar), preferably at normal pressure.

The compounds of the general formula (II) are known per se or can be prepared by a customary method [compare EP-A 2143,746].

The compounds of the general formula (III) are known per se [compare, for example, EP-A2 236,734, U.S. Pat. No. 4,758,584, EP-A2 143,746].

The compounds of the general formula (IV) are known per set or can be prepared by a customary method [compare Houben-Weyl, Methoden der organischen Chemie, Synthese von Peptiden II (Methods in Organic Chemistry, Synthesis of Peptides II), 4th edition, vol. 15/1, 15/2, Georg Thieme Verlag, Stuttgard].

The reaction with the compounds of the general formula (IV) and the introduction of the amino acid group A, B, D and L is in general carried out by reaction of an appropriate fragment, consisting of one or more amino acid groups, with a free carboxyl group, which may be present in activated form, with a complementary fragment, consisting of one or more amino acid groups, having an amino group, if appropriate in activated form, and by optionally repeating this procedure with appropriate fragments until the desired peptides of the abovementioned generally formulae have been prepared, and subsequently optionally removing protecting groups or exchanging them for other protecting groups.

Auxiliaries employed for the respective peptide couplings are preferably condensing agents which may also be bases, in particular if the carboxyl group is present in activated form as the anhydride. The customary condensing agents such as carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride, N-cyclohexyl-N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium-3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosponium hexafluorophosphate or 1-hydroxybenzotriazole are preferred here.

In addition, for example, alkali metal carbonates, for example sodium carbonate or potassium carbonate or sodium hydrogen carbonate or potassium hydrogen carbonate, or organic bases such as trialkylamines, for example triethylamine, N-ethylmorpholine, N-methylpiperidine or N-methylmorpholine can be employed. Triethylamine is preferred.

The auxiliaries and bases are employed in an amount of from 1.0 mol to 3.0 mols, preferably 1.0 to 1.2 mols, relative in each case to 1 mol of the compounds of the general formula (IV) or (V).

The peptide couplings are carried out in a temperature range from 0° C. to 100° C., preferably at 10 to 50° C. and at normal pressure.

The reactions can be carried out both at normal pressure and at elevated or reduced pressure (for example 0.5 to 5 bar), preferably at normal pressure.

The removal of the respective protecting groups from the individual peptide linkages is carried out in a manner known per se under acidic or basic conditions, or reductively by catalytic hydrogenation, for example using Pd/C in organic solvents such as ethers, for example tetrahydrofuran or dioxane, or alcohols, for example methanol, ethanol or isopropanol [compare Protective Groups in Organic Synthesis, W. Greene, John Wiley & Sons, New York, 1981; Chemistry and Biochemistry of the Amino Acids, G. C. Barrett, Chapman and Hall, London, New York, 1985].

The compounds of the general formulae (V) and (VI) are known or can be prepared by a customary method.

It has surprisingly been found that the compounds of the general formula (I) have exceptionally strong action against retroviruses. This is proved by an HIV-specific protease enzyme test.

The results of the examples shown below were determined by the HIV test system described in the following references [compare Hansen, J., Billich, S., Schulze, T., Sukro, S. and Mölling, K. (1988), EMBO Journal, Vol. 7, No. 6, pp. 1785-1791]: purified HIV protease was incubated with synthetic peptide which imitates a cleavage site in the Gag precursor protein and represents an in vivo cleavage site of the HIV protease. The resulting cleavage products of the synthetic peptide were analyzed by means of Reverse Phase High Performance Liquid Chromatography (RP-HPLC). The $IC_{50}$ values indicated relate to the substance concentration which causes a 50% inhibition of the protease activity under the abovementioned test conditions.

| Example No. | $IC_{50}$ (RP-HPLC) |
|---|---|
| I | $5 \times 10^{-7}$ M |
| II | $5 \times 10^{-8}$ M |
| III | $5 \times 10^{-9}$ M |
| IV | $10^{-7}$ M |
| V | $5 \times 10^{-8}$ M |
| VIa | $10^{-9}$ M |
| VIb | $10^{-9}$ M |
| VIIa | $10^{-9}$ M |

The compounds according to the invention additionally showed potent antiviral activity in the HIV-I infected cell culture on freshly prepared peripheral human blood lymphocytes (PBL's). The HIV-Test was performed basically according to the method described by Pauwels et al., Journal of Virological Methods 20, 309 (1988).

| Example No. | $IC_{50}$* (μg/ml) |
|---|---|
| VIa | 0,40 |
| VIb | 0,09 |
| VIIa | 1,00 |
| VIIb | 3,00 |

*$IC_{50}$ = 50% inhibitory concentration

The compounds according to the invention are valuable active compounds in human and veterinary medicine for the treatment and prophylaxis of disorders caused by retroviruses.

Examples of indication areas which may be mentioned in human medicine are:

1.) The treatment or prophylaxis of human retrovirus infections.

2.) For the treatment or prophylaxis of diseases caused by HIV I (human immunodeficiency virus; earlier called HTLV III/LAV) and HIV II (AIDS), and the stages associated with this such as ARC (AIDS-related complex) and LAS (lymphadenopathy syndrome), and also the immunodeficiency and encephalopathy caused by this virus.

3.) For the treatment or the prophylaxis of an HTLV I or HTLV II infection.

4.) For the treatment or the prophylaxis of the HIV-carrier state (HIV-transmitter state).

Examples of indications in veterinary medicine which may be mentioned are: Infections with a) Maedi-visna (in sheep and goats)

b) progressive pneumonia virus (PPV) (in sheep and goats)

c) caprine arthritis encephalitis virus (in sheep and goats)

d) Zwoegerziekte virus (in sheep)

e) infectious anaemia virus (of the horse)

f) infections caused by the feline leukaemia virus g) infections caused by the feline immunodeficiency virus In human medicine, the abovementioned items 2, 3 and 4 are preferred from the indication area.

The present invention includes pharmaceutical preparations which contain one or more compounds of the formula (I) or which consist of one or more active compounds of the formula (I) in addition non-toxic inert, pharmaceutically suitable excipients, and processes for the production of these preparations.

The active compounds of the formula (I) should be present in the abovementioned pharmaceutical preparations in a concentration of about 0.1 to 99.5, preferably about 0.5 to 95, % by weight of the total mixture.

The abovementioned pharmaceutical preparations may also contain further pharmaceutically active compounds in addition to the compounds of the formula (I).

The abovementioned pharmaceutical preparations are prepared in the customary manner by known methods, for example by mixing the active compound or compounds with the excipient or excipients.

In general, it has proved advantageous both in human and in veterinary medicine to administer the active compound or compounds of the formula (I) in total amounts of about 0.5 to about 500, preferably 5 to 100, mg/kg of body weight every 24 hours, if desired in the form of several individual doses, in order to achieve the desired results. An individual dose preferably contains the active compound or compounds in amounts from about 1 to about 80, in particular 1 to 30, mg/kg of body weight. However, it may be necessary to deviate from the dosages mentioned, in particular depending on the species and the body weight of the subject to be treated, the nature and the severity of the disease, the manner of preparation and administration of the medicament and the period or interval within which administration takes place.

Addendum to the Experimental Section

I. List of the thin layer systems used:

| | | |
|---|---|---|
| Ia | $CH_2Cl_2/CH_3OH$ | 90:10 |
| Ib | $CH_2Cl_2/CH_3OH$ | 95:5 |
| Ic | $CH_2Cl_2/CH_3OH$ | 85:15 |
| II | $CH_2Cl_2$ | |
| IIIa | $CH_2Cl_2/CH_3OH/CH_3COOH/H_2O$ | 65:25:3:4 |
| IIIb | $CH_2Cl_2/CH_3OH/H_2O$ | 65:25:4 |
| IV | $CH_2Cl_2/CH_3OH/CH_3COOH$ | 90:10:0.1 |
| V | Petroleum ether (b.p. 60–90° C.)/diethyl ether | 1:1 |
| VI | Toluene/ethyl acetate | 4:1 |
| VII | Toluene/ethyl acetate | 6:1 |
| VIII | Toluene/ethyl acetate | 2:1 |
| IX | Hexane/ethyl acetate | 4:1 |

II. Amino acids

In general, the indication of the configuration is carried out by placing an L or D in front of the amino acid abbreviation, and in the case of the racemate a D,L- where, for simplification, the configuration indication can be suppressed in the case of L-amino acids and explicit indication then only takes place in the case of the D-form or the D,L-mixture.

| | |
|---|---|
| Ala | L-alanine |
| Arg | L-arginine |
| Asn | L-asparagine |
| Asp | L-aspartic acid |
| Cys | L-cysteine |
| Gln | L-glutamine |
| Glu | L-glutamic acid |
| Gly | L-glycine |
| His | L-histidine |
| Ile | L-isoleucine |

-continued

| | |
|---|---|
| Leu | L-leucine |
| Lys | L-lysine |
| Phe | L-phenylalanine |
| Ser | L-serine |

III. Activation reagents

| | |
|---|---|
| HOBT | 1-hydroxybenzotriazole |
| HOSU | N-hydroxysuccinimide |
| DCC | dicyclohexylcarbodiimide |
| Morpo-CDI | N-cyclohexyl-N'-(2-morpholinoethyl)carbodiimide metho-p-toluenesulphonate |
| BOP | benzotriazolyloxy-tris(dimethylamino)phosponium hexafluorophosphate |

IV. Protecting groups (hydroxyl, amino)

| | |
|---|---|
| Bzl | benzyl |
| tBu | tert.butyl |
| Boc | tert.butylcarbonyl |
| Z | benzyloxycarbonyl |
| Fmoc | 9-fluorenylmethoxycarbonyl |
| AMP | 2-aminomethylpyridine |
| AEP | 2-aminoethylpyridine |
| BOM | benzyloxymethylene |

EXAMPLE 1

Starting Compounds

N-(Benzyloxycarbonyl)-2(S)-amino-3-cyclohexylpropionic acid

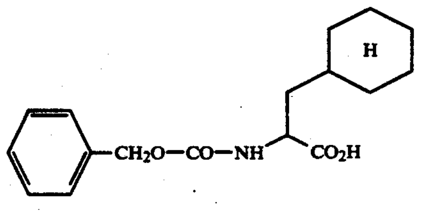

290 g (1.7 mol) of 2-amino-3-cyclohexylpropionic acid are dissolved in 375 ml of 4N NaOH. The solution is made up to 2 l with water and 500 ml of dioxane are added. 255 ml (1.7 mol) of benzyloxycarbonyl chloride are added dropwise at pH 10 under pH-state conditions. After 8 h, the solution is extracted twice using diethyl ether and acidified to pH 2 using 1N hydrochloric acid. The product is extracted 3 times using 200 ml of ethyl acetate each time. After washing the organic extract, drying over sodium sulphate and concentrating, 5 g of the title compound are obtained.

TLC: $R_f$(IIIa)=0.81 (TDM)*

MS (EI): 305

Empirical formula (MW): $C_{17}H_{23}NO_4$ (305.374)

TDM=N,N,N',N'-Tetramethyl-4,4'-diaminodiphenylmethane

EXAMPLE 2

Methyl-N-methyl-[2-(S)-(benzyloxycarbonyl)-amino-3-cyclohexylpropionyl]hydroxamate

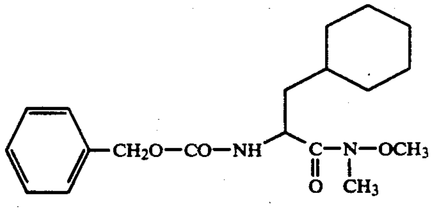

305 g (1 mol) of the compound from Example 1 and 107.2 g (1.1 mol) of N,O-dimethylhydroxylamine hydrochloride are dissolved in 2000 ml of dichloromethane and 725 ml (6 mol) of N-methylpiperidine are added at 0° C. 590 ml (1.2 mol) of n-propylphosphoric anhydride are added dropwise at −20° C. After stirring at room temperature for 12 h, the mixture is concentrated and the residue is partitioned against sodium bicarbonate solution using ethyl acetate. The organic phase is washed once with potassium hydrogen sulphate and twice with sodium chloride solution. After drying over sodium sulphate and concentrating, 240 g (69% of theory) of the title compound are obtained.

TLC: $R_f$(Ib)=0.67 (TDM)

MS (DCI)=349

Empirical formula (MW): $C_{19}H_{28}N_2O_4$ (348.21)

$^1$H-NMR (DMSO-$d_6$): δ=0.7–1.8 (m, 13H); 3.1 (s, 3H); 3.7 (s, 3H); 4.55 (t, 1H); 5.0 (s, 2H); 7.3 (m, 5H); 7.55 (d, 1H) ppm.

EXAMPLE 3

2(S)-(Benzyloxycarbonyl)amino-3-cyclohexylpropanal

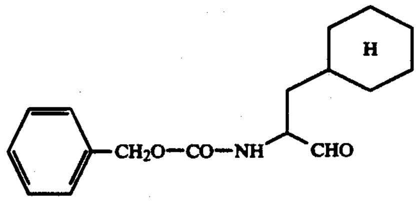

230 g (0.66 mol) of the compound from Example 2 are dissolved in 1000 ml of dried diethyl ether under nitrogen and 780 ml of a 1N solution of lithium aluminum hydride in diethyl ether are added dropwise at 0° C. After completion of the addition, the mixture is subsequently stirred at 0° C. for 45 minutes and then cautiously acidified with a 5% strength solution of potassium hydrogen sulphate. The aqueous phase is separated off and back-extracted twice with diethyl ether. The combined organic phases are washed 3 times with 0.5M potassium hydrogen sulphate solution, 3 times with saturated sodium hydrogen carbonate solution and twice with sodium chloride solution. After drying over sodium sulphate and concentrating, 193 g of the title compound are obtained in slightly impure form. The compound must be stored at −20° C. and immediately further reacted if possible.

TLC: $R_f$(Ib)=0.36 (TDM, 2,4-dinitrophenylhydrazine)

MS (EI)=289

IR=1710, 2850, 2900 $cm^{-1}$

Empirical formula (MW): $C_{17}H_{23}NO_3$ (289.18)

$^1H$-NMR (DMSO-$d_6$): $\delta = 9.5$ (s, 1H) ppm.

EXAMPLE 4

2'(S)-(Benzyloxycarbonyl)amino-but-3'-en-yl-cyclohexane

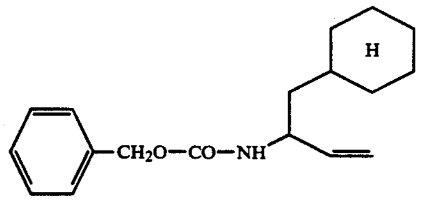

274.6 g (0.66 mol) of Instant-Ylid ® are stirred in 500 ml of absolute tetrahydrofuran for 30 minutes. 190.86 g (0.66 mol) of the compound from Example 3 are dissolved in 400 ml of absolute tetrahydrofuran and added dropwise with ice-cooling to the ylid suspension. The mixture is subsequently stirred at room temperature for 12 h. The suspension is poured on to 1000 ml of ice and extracted 4 times using petroleum ether (b.p. 60°-90° C.). After washing the organic phase with sodium chloride solution and drying over magnesium sulphate, 190 g of the title compound are obtained.

TLC: $R_f$(II)=0.49 (TDM, $I_2$)

TLC: $R_f$(Ia)=0.93

MS (DCI)=288

Empirical formula (MW): $C_{18}H_{25}NO_2$ (287.19)

$^1H$-NMR (DMSO-$d_6$): $\delta = 0.8$-1.8 (m, 13H); 4.05 (t, 1H); 5.0 (D+m, 4H); 5.7 (m, 1H); 7.3 (m, 5+1H) ppm.

EXAMPLE 5 AND EXAMPLE 6

2(R)-{1(S)-[1-Benzoxycarbonyl)amino-2-cyclohexyl]-ethyl}-oxirane (Example 5)

2(S)-{1(S)-[1-Benzoxycarbonylamino-2-cyclohexyl]-ethyl}-oxirane (Example 6)

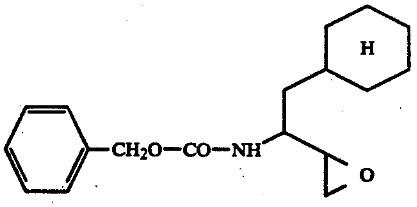

189.55 g (0.66 mol) of the compound from Example 4 are dissolved in 600 ml of dichloromethane and 227.79 g (1.32 mol) of 3-chloroperoxybenzoic acid are added in portions at 0° C. After stirring for 12 h, the solution is washed 3 times with saturated sodium sulphate solution and 3 times with saturated sodium carbonate solution. After drying and concentrating, 278.3 g of an oil are obtained. The crude product is chromatographed on silica gel [column 30×10 cm, petroleum ether (b.p. 60°-90° C.); diethyl ether (2:1]. The first fraction contains 3-chlorobenzoic acid. 52.04 g of the title compound are obtained in fraction 2.

TLC: $R_f$(V)=0.53

MS (DCI)=304

Empirical formula (MW): $C_{18}H_{25}NO_3$ (303.2)

1H-NMR ($CDCl_3$): $\delta = 0.8$-1.9 (m, 13H); 2.55 (t, 1H); 2.7 (6, 1H); 2,95 (s, 1H); 4.0 (q, 1H); 4.7 (d, 1H); 5.1 (s, 2H); 7.3 (m, 5H) ppm.

36.82 g of the title compound (Example 6) are obtained as fraction 3 of the column chromatography.

TLC: $R_f$(V)=0.45

MS (DCI)=304

Empirical formula: $C_{18}H_{25}NO_3$

EXAMPLE 7

3(S)-(Benzyloxycarbonyl)amino-4-cyclohexyl-2(S)-hydroxyl-1-iodobutane

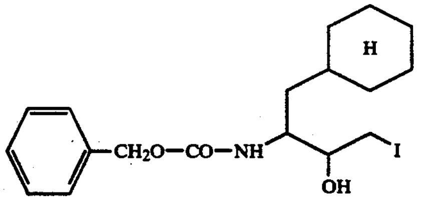

52.04 g (172 mmol) of the compound from Example 5 are dissolved in 400 ml of acetonitrile and 25.82 g (172 mmol) of sodium iodide are added at 0° C. 22.3 ml (172 mmol) of trimethylchlorosilane are added dropwise in the course of 30 at 0° C. The mixture is subsequently stirred at 0° C. for 1 h. The suspension is poured on to 1000 ml of ice-water and extracted 3 times using 200 ml of diethyl ether each time. After washing the organic phase with 0.1M thiosulphate solution and sodium chloride solution, it is dried over sodium sulphate and concentrated. The crude product (66.8 g of an oil) is chromatographed on a flash column (20×10 cm, dichloromethane). The O—Si$(CH_3)_3$ derivative is obtained as a by-product which can be cleaved to give the title compound by treating with aqueous potassium fluoride solution.

57.5 g of a colorless oil are obtained.

TLC: $R_f$(Ib)=0.60

TLC: $R_f$(VI)=0.49

MS (EI)=431

Empirical formula (MW): $C_{18}H_{26}NO_3I$ (431.1)

EXAMPLE 8

3-Benzyloxycarbonyl-4(S)-cyclohexylmethyl-2,2-dimethyl-5(S)-iodomethyl-oxazolidine

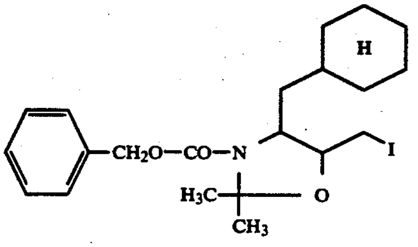

57.6 g (113 mmol) of the compound from Example 7 are dissolved in 230 ml of dimethylformamide. After adding 200 mg (1.16 mmol) of para-toluenesulphonic acid, 19.2 g (266 mmol) of 2-methoxypropene are added dropwise and the solution is heated at 80° C. for 12 h. After cooling, the residue is taken up in a 1:1 mixture of petroleum ether (b.p. 60°-90° C.) and dichloromethane and flash-chromatographed 3 times using saturated sodium hydrogen carbonate solution [400 g of silica gel, petroleum ether (b.p. 60°-90° C.): dichloromethane (1:1)]. 54.7 g of a white solid are obtained.

TLC: $R_f$(IX)=0.53 (TDM, $I_2$)

M.P.: substance contains wax

MS (FAB)=472

Empirical formula (MW): $C_{21}H_{30}NO_3I$ (471.38)

$^1$H-NMR (DMSO-$d_6$): δ=0.8-1.8 (m, 13H); 1.3 (s, 3H); 1.4 (s, 3H); 3.3 (t, 1H); 3.45 (t, 1H); 3.95 (m, 1H); 4.05 (m, 1H); 5.1 (9, 2H); 7.3 (m, 5H) ppm.

EXAMPLE 9

3-Benzyloxycarbonyl-4(S)-cyclohexylmethyl-2,2-dimethyl-5(S)-[1'-(2',2'-bismethoxycarbonyl)ethyl]oxazolidine

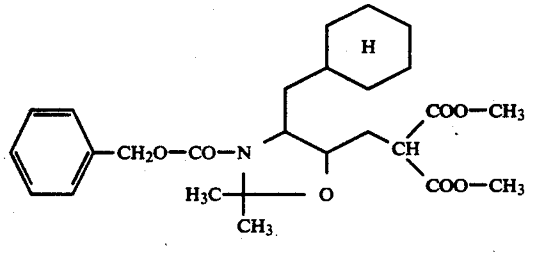

11.96 ml (104.4 mmol) of dimethyl malonate are stirred in 160 ml of dried dimethoxymethane under nitrogen and 3.13 g (104.4 mmol) of sodium hydride (80% pure) are added. After 10 minutes at room temperature, 41.1 g (87 mmol) of the compound from Example 8 are added. After 12 h under reflux (140° C.), the mixture is cooled and excess hydride in quenched using 1N citric acid. After concentrating, the residue is taken up in ethyl acetate, washed 3 times with water, dried over sodium sulphate and concentrated. 38.2 g of an oil are obtained. Chromatography on silica gel (toluene-/ethyl acetate 100:0→50:50) yields 27.64 g of the title compound in fraction 2. 3 g of starting material are recovered as fraction 1.

TLC: $R_f$(VII)=0.48

TLC: $R_f$(VIII)=0.34

MS (DCI): 476.2

Empirical formula (MW): $C_{26}H_{37}NO_7$ (475.26)

EXAMPLE 10

3-Benzyloxycarbonyl-4(S)-cyclohexylmethyl-2,2-dimethyl-5(S)-[1'-(2',2'-bismethoxycarbonyl-3'-methyl)-butyl]oxazolidine

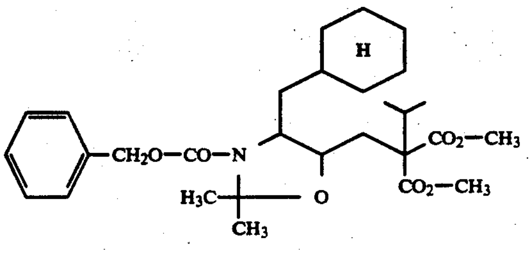

1.87 g (62.5 mmol) of sodium hydride (80% pure) are suspended in 100 ml of dried tetrahydrofuran under nitrogen. A solution of 27 g (56.8 mmol) of the compound from Example 9 in 50 ml of tetrahydrofuran is added dropwise to this suspension. After 20 minutes at reflux temperature, 56.81 ml (568 mmol) of isopropyl iodide are added dropwise. The solution is heated under reflux for 12 h. After cooling, it is stirred with 1N citric acid until it gives an acid reaction, and the solvent is replaced by ethyl acetate. After drying over sodium sulphate and concentrating, the crude product is purified on a silica gel column [petroleum ether (b.p. 60°-90° C.): diethyl ether (1:1)]. 25.94 g of a pale yellow oil are obtained.

TLC: $R_f$(VII=0.59

TLC: $R_f$(VIII)=0.48

MS (DCI)=518

Empirical formula (MW): $C_{29}H_{43}NO_7$ (517.28)

EXAMPLE 11

'-Benzyloxycarbonyl-4-(S)-cyclohexylmethyl-2,2-dimethyl-5(S)-[1'-(2'-carboxy-3'-methyl)butyl]oxazolidine

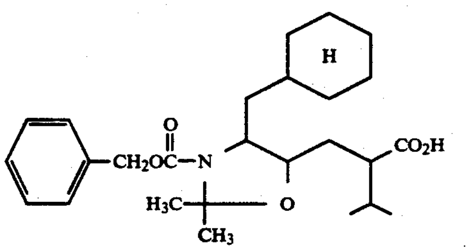

25.9 g (50.1 mmol) of the compound from Example 10 are dissolved in 200 ml of methanol, 150.2 ml (300.4 mmol) of 2N NaOH are added and the mixture is heated under reflux for 96 h. After cooling and concentrating, the residue is taken up in water, extracted 3 times with diethyl ether and, after acidifying to pH 2, extracted 3 times with ethyl acetate. The ethyl acetate phase is washed until neutral, dried and concentrated. 21.3 g of a white foam are obtained.

TLC: $R_f$(IV)=0.79

MS (⊖FAB)=444

Empirical formula (MW): $C_{26}H_{39}NO_5$ (445.6)

EXAMPLE 12

3-Benzyloxycarbonyl-4-(S)-cyclohexylmethyl-2,2-dimethyl-5(S)-{1'-[2'-(carbonyl(S)-isoleucinyl-2-pyridylmethylamidyl)-3'-methyl]butyl}oxazolidine

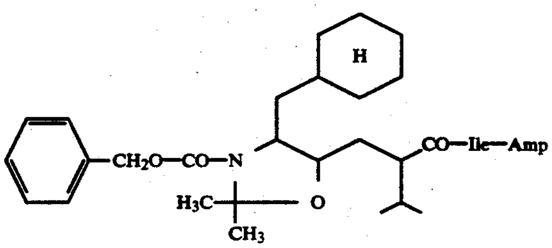

8 g (18 mmol) of the compound from Example 11 and 3.63 g (19 mmol) of HOBT are dissolved in 50 ml of dichloromethane and cooled to 0° C. 3.92 g (19 mmol) of dicyclohexylcarbodiimide are dissolved in 30 ml of dichloromethane and added. After 1 h at 0° C., dicyclohexylurea has precipitated.

5.88 g (20 mmol) of S-isoleucinyl-2-pyridylmethylamide dihydrochloride are dissolved in 50 ml of dichloromethane and 5.46 ml (45 mmol) of N-methylpiperidine are added. After 1 h with stirring, the white suspension is added to the above suspension and the mixture is stirred for 24 h. The reaction is stopped by addition of 100 μl of glacial acetic acid and the solvent is removed in vacuo. The residue is thoroughly stirred with ethyl acetate at 0° C., and the urea is filtered off with suction and washed. After drying over sodium sulphate, 12 g of a yellow oil are obtained which is chromatographed on silica gel [$CH_2Cl_2$/methanol (95:5)]. 10 g of the title compound are obtained.

TLC: $R_f$(Ia)=0.63 f

MS (FAB)=649

Empirical formula (MW): $C_{38}H_{56}N_4O_5$ (648.4)

EXAMPLE 13

Nα-{1-[5-(S)-Amino-6-cyclohexyl-4(S)-hydroxy-2-(1-methyl)-erthyl]hexanoyl}(S)-isoleucinyl-2-pyridylmethylamide

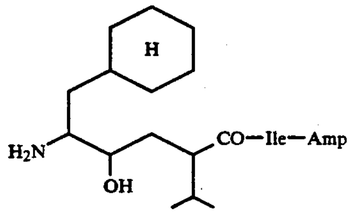

7 g ((10.8 mmol) of the compound from Example 12 are dissolved in 120 ml of methanol and 10 ml of glacial acetic acid and 200 mg of palladium on active carbon added. A stream of $H_2$ is passed through the solution for 10 h, then it is filtered off through celite with suction and 50 ml of potassium hydrogen sulphate solution are added. After removing the methanol by distillation, the residue is diluted with 80 ml of water and extracted twice using ethyl acetate. The aqueous solution is brought to pH 10 with 2N NaOH and extracted 3 times using ethyl acetate. After drying and concentrating the organic phase, 3.2 g of a wax-like solid are obtained.

TLC: $R_f$(IIIa)=0.80

MS (FAB)=475

Empirical formula (MW): $C_{27}H_{46}N_4O_3$ (474.3)

EXAMPLE 14

Nα-{Nδ-[Nα-(1,1-dimethylethoxycarbonyl)-(S)-asparaginyl]-1-[5-(S)-amino-6-cyclohexyl-4-(S)-hydroxy-2-(1methyl)ethyl]-hexanoyl}-(S)-isoleucinyl-2-pyridylmethylamide

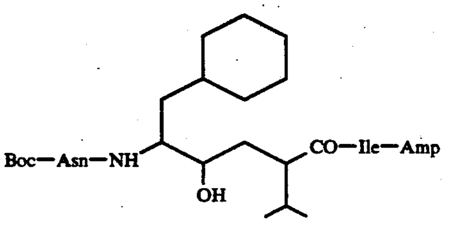

255 mg (1.1 mmol) of Nα-1,1-dimethylethoxycarbonylasparagine are dissolved in 5 ml of diemthylformamide and 110 μl (1 mmol) of N-methylpiperidine are added. After cooling to −20° C., 136 mg (1mmol) of isobutyl chloroformate are added. After preactivation for 15 minutes, 474 mg (1 mmol) of the compound from Example 13, dissolved in 5 ml of dimethyl formamide and 110 μl of N-methylpiperidine, are slowly added. After stirring at room temperature for 3 h, the reaction is quenched by addition of saturated sodium hydrogen carbonate solution and the mixture is concentrated. The residue is taken up in ethyl acetate and washed twice with saturated sodium hydrogen carbonate solution and with sodium chloride solution, dried and concentrated. After HPLC (30% acetonitrile→60% acetonitrile, 0.05% TFA), 10 mg of the desired compound are obtained.

TLC: $R_f$(IIIa)=0.90

MS (FAB)=689

Empirical formula (MW): $C_{36}H_{60}N_5)_7$(688.3)

EXAMPLE 15

Nα-{Nδ-[Nα-phenylmethoxycarbonyl-(S)-asparaginyl]-1-[5-(S)-amino-6-cyclohexyl-4-(S)-hydroxy-2-(1-methyl)ethyl]-hexanoyl}-(S)-isoleucinyl-2-pyridylmethylamide

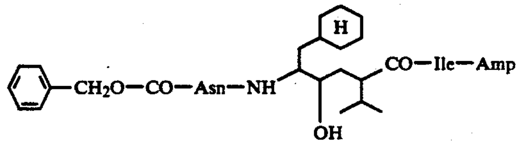

781 mg (2.83 mmol) of Nα-phenylmethoxycarbonyl(S)-asparagine are dissolved in 20 ml of dimethylformamide and 451 mg (2.83 mmol) of 1-hydroxybenzotriazole are added. After cooling to −10° C., 1.24 g (2.93 mmol) of N-cyclohexyl-N'-(2-morpholinoethyl)-carbodiimide metho-p-toluenesulphonate (morpho-CDI) are added. 1.26 g (2.67 mmol) of the compound from Example 13 are dissolved in 10 ml of dimethylformamide and 355 μl (2.93 mmol) of N-methylpiperidine are added and this solution is then added dropwise to the above solution. The mixture is stirred at room temperature for 12 h and concentrated, and the residue is digested with water and then with ethyl acetate. 660 mg of the title compound are obtained.

TCL: $R_f$(Ic)=0.55

Empirical formula (MW): $C_{39}H_{58}N_6O_7$ (722.9)

EXAMPLE 16

Nα-{Nδ-[(S)-Asparaginyl]-1-[(5-(S)-amino-6-cyclohexyl-4-(S)-hydroxy-2-(1-methyl)ethyl]hexanoyl}-(S)-isoleucinyl-2-pyridylmethylamide

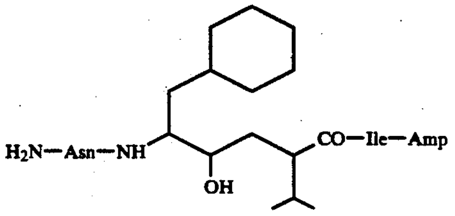

660 mg (0.914 mmol) of the compound from Example 15 are dissolved in 50 ml of methanol and 100 mg of palladium hydroxide are added. After passage of $H_2$ for 6 h, the solution is filtered off through celite with suction and concentrated. 600 mg of the title compound are obtained.

TLC: $R_f$(Ic)=0.44

MS (FAB)=589

Empirical formula (MW): $C_{31}H_{52}N_6O_5$ (588.8)

EXAMPLE 17

Nα-{Nδ-{Nα-(Nα-phenylmethoxycarbonyl-(S)-phenylalaninyl)-(S)-asparaginyl}-1-[5-(S)-amino-6-cyclohexyl-4-(S)-hydroxy-2-(1-methyl)ethyl]hexanoyl}-(S)-isoleucinyl-pyridylmethylamide

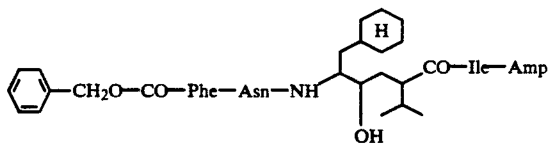

341. mg (1.15 mmol) of N-phenylmethoxycarbonyl-(S)-phenylalanyl, 117.5 mg (1.14 mmol) of 1-hydroxybenzotriazole, 483.7 mg (1.142 mmol) of morpho-CDI, 537 mg (0.91 mmol) of the compound from Example 16 and 138 μl of N-methylpiperidine are reacted in accordance with Example 15 to give the title compound. 540 mg are obtained.
TLC: $R_f$(Ic)=0.58
Empirical formula (MW): $C_{48}H_{67}N_7O_8$ (870.1)

EXAMPLE 18

Nα-{Nδ-[Nα-((S)-phenylalanyl)-(S)-asparaginyl]-1-[5-(S)-amino-6-cyclohexyl-4-(S)-hydroxy-2-(1-methyl)ethyl]hexanoyl}-(S)-isoleucinyl-2-pyridylmethylamide

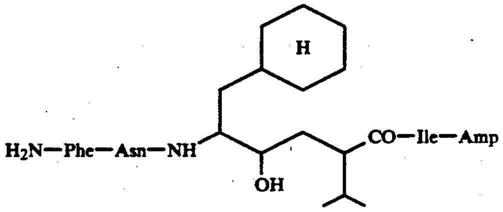

540 mg (62.1 mmol) of the compound from Example 17 are dissolved in 50 ml of methanol and 100 mg of palladium hydroxide are added. After hydrogenation at room temperature for 6 h, the solution is filtered off with suction on a filter layer, subsequently washed twice with hot methanol and concentrated. After chromatography on a silica gel column [100% $CH_2Cl_2$→$CH_2Cl_2/CH_3OH$ (93:7)], 371 mg of the title compound are obtained.
TLC: $R_f$(Ic)=0.58
MS (FAB+L)=742
Empirical formula (MW): $C_{40}H_{51}N_7O_5$ (735.4)

EXAMPLE 19

Nα-{Nδ-{Nα-[Nα-(1,1,-dimethylethoxycarbonyl)-(S)-phenylalaninyl]-(S)-asparaginyl}-1-[5-(S)-amino-6-cyclohexyl-4-(S)-hydroxy-2(1-methyl)ethyl]hexanoyl}-(S)-isoleucinyl-2-pyridylmethylamide

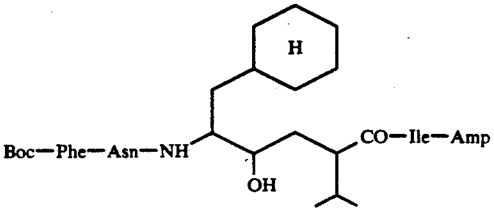

37 mg (0.044 mmol) of the compound from Example 18 are dissolved in 5 ml of dimethylformamide and 30 mg (0.14 mmol) of bis(1,1-dimethylethyl) pyrocarbonate are added. The solution is rendered alkaline using a few drops of triethylamine. After 2 h at room temperature, the solution is concentrated and triturated with diethyl ether. 10 mg of the title compound are obtained.
TLC: $R_f$(IIIb)=0.70
MS (FAB)=836
Empirical formula (MW): $C_{45}H_{69}N_7O_8$ (835.4)

EXAMPLE 20

Nα-{δ-{Nα-[Nα-(1,1-dimethylethoxycarbonyl)-(S)-seryl]-(S)-phenylalaninyl}-(S)-asparaginyl}-1-5-(S)-amino-6-cyclohexyl-4-(S)-hydroxy-2-(1-methyl)ethyl]-hexanoyl}-(S)-isoleucinyl-2-pyridylmethylamide

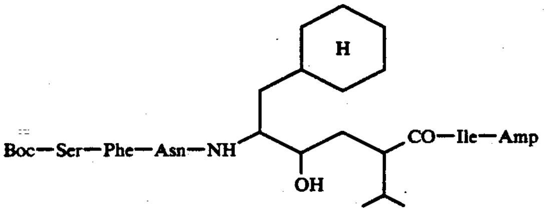

40 mg (192 μmol) of Nα-(1,1-dimethylethoxycarbonyl)-(S)-serine, 31.1 mg (200 μmol) of 1-hydroxybenzotriazole, 85 mg (200 μmol) of morpho-CDI and 120 mg (160 μmol) of the compound from Example 18 are reacted in 8 ml of dimethylformamide in accordance with Example 15 to give the title compound.
Yield: 130 mg
TLC: $R_f$(Ic)=0.63
MS (FAB=923
MS (FAB+Li)=929
MS (FAB+Na)=945
Empirical formula (MW): $C_{48}H_{74}N_8O_{10}$ (923.1)

EXAMPLE 21

Boc—Aib—Phe—Val—$OCH_3$ 10.83 g (52.5 mmol) of DCC were added to a stirred solution, cooled to 0° C., of 10.17 g (50.0 mmol) of 2-(1,1-dimethylethoxycarbonyl)amino-2-methyl-propionic acid and 7.09 g (52.5 mmol) of HOBT in 140 ml of anhydrous dichloromethane. The cooling bath was removed and the mixture was stirred at room temperature for 30 min. It was then cooled to 0° C. again, a solution of 17.47 g (55.5 mol) of HCl.H—Phe—Val—$OCH_3$ and 13.75 ml (125.0 mmol) of N-methylmorpholine in 140 ml of dichloromethane was added and the mixture was subsequently stirred in a thawing ice bath for 15 h. The precipitated urea was separated off by filtration, and the filtrate was washed with 2×100 ml of $NaHCO_3$ solution and 100 ml of water and dried over $MgSO_4$. After evaporating the solvent in vacuo and chromatography of the crude product on 270 g of silica gel (toluene:ethyl acetate 3:2), 20.0 g (86%) of the title compound were obtained as a colorless foam.
TLC: $R_f$=0.38 (toluene:ethyl acetate 1:1)
MS (DCI, $NH_3$) m/Z=464 $(M+H)^+$
Empirical formula (MW): $C_{24}H_{37}H_3O_5$ (463.58)

EXAMPLE 22

Boc—AiB—Phe—Val—OH

A solution of 2.35 g (56.0 mmol) of lithium hydroxide hydrate in 55 ml of water was added to a solution of 13.0 g (28.0 mmol) of the compound from Example 21 in 10 ml of THF and the mixture was stirred at 0° C. for 3 h.

The reaction mixture was then poured into a mixture of 60 ml of water, 40 g of ice and 100 ml of ethyl acetate and adjusted to pH 3 by adding 1N hydrochloric acid. The organic phase was separated off, the aqueous phase was extracted with 50 ml of ethyl acetate and the combined organic extracts were dried over magnesium sulphate. After evaporating the solvent in vacuo and treating the residue with 10 ml of ether and 30 ml of n-pentane, 10.3 g (82% of theory) of the title compound were obtained as colorless crystals.

M.p.: 157° C.

HPLC purity: >96%

TLC: $R_f$=0.44 (acetonitrile:water=9.1)

MS (FAB) m/Z=350 (M+H)+, 472 (M+Na)+

Empirical formula (MW): $C_{23}H_{35}N_3O_6$ (449.55)

EXAMPLE 23

Boc—AiB—Val—OCH3

As described for Example 21, 10.3 g (79%) of the title compound were obtained as colorless crystals from 10.17 g (50.0 mmol) of 2-(1,1-dimethylethoxycarbonyl-)amino-2-methyl-propionic acid and 9.19 g (55.5 mmol) of HCl.H—Val—$OCH_3$ after chromatography of the crude product on 300 g of silica gel (toluene:ethyl acetate 1:1).

M.p.: 108° C.

TLC: $R_f$=0.43 (toluene:ethyl acetate 1:1)

MS (FAB) m/Z=317 (M+H)+.

Empirical formula (MW): $C_{15}H_{28}N_2O_5$ (316.40).

EXAMPLE 24

Boc—AiB—Val—OH

As described for Example 22, 4.0 g (84%) of the title compound was obtained as a colorless powder from 5.0 g (15.8 mmol) of the compound from Example 23.

M.p.: 162° C.

TLC: $R_f$=0.5 (acetonitrile:water 9:1)

MS (FAB) m/Z=309 (M+Li)+, 617 (2M+2Li—H)*

Empirical formula (MW): $C_{14}H_{26}N_2O_5$ (302.38).

EXAMPLE 25

Boc—Aib—Ser—Phe—Val—OCH3

As described for Example 21, 203 mg (72%) of the title compound were obtained as a pale powder from 104 mg (0.51 mmol) of 2-(1,1-dimethylethoxycarbonyl)-amino-2-methyl-propionic acid and 226 mg (0.56 mmol) of HCl.H—Ser—Phe—Val—$OCH_3$ after chromatography of the crude product on 40 g of silica gel (toluene:ethyl acetate 1:9)

M.p.: from 82° C. (dec.)

TLC: $R_f$=0.24 (ethyl acetate)

MS (FAB) m/Z=551 (M+H)+, 573 (M+Na)+.

Empirical formula (MW): $C_{27}H_{42}N_4O_8$ (550.66).

EXAMPLE 26

Boc—AiB—Ser—Phe—Val—OH

As described for Example 22, 2.311 g (84%) of the title compound were obtained as a pale powder from 2.802 g (5.10 mmol) of the compound from Example 25.

M.p.: from 137° C. (dec.)

TLC: $R_f$=0.31 (acetonitrile:water 9:1)

MS (FAB) m/Z=543 (M+Li)+, 559 (M+2Li)+.

Empirical formula (MW): $C_{26}H_{40}N_4O_8$ (536.64).

EXAMPLE 27

Boc—Aib—Ser—Phe—OCH3

As described for Example 21, 3.92 g of the title compound were obtained as colorless crystals from 2.03 g (10.0 mmol) of 2-(1,1-dimethylethoxycarbonyl)-amino-2-methyl-propionic acid and 3.35 g (11.1 mmol) of HCl.H—Ser—Phe—$OCH_3$ after chromatography of the crude product on 100 g of silica gel (ethyl acetate).

M.p.: 123°-125° c.

TLC: $R_f$=0.31 (ethyl acetate)

MS (DCI, $NH_3$) m/Z=452 (M+H)+.

Empirical formula (MW): $C_{22}H_{33}N_3O_7$ (451.53).

EXAMPLE 28

Boc—AiB—Ser—Phe—OH

As described for Example 22, 2.35 g (62%) of the title compound were obtained as a pale foam from 3.90 g (8.64 mmol) of the compound from Example 27.

TLC: $R_f$=0.25 (acetonitrile:water 9:1)

MS (FAB) m/Z=438 (M+H)+, 460 (M+Na)+.

Empirical formula (MW): $C_{21}H_{31}N_3O_7$ (437.50).

EXAMPLE 29

Boc—AiB—Pro—Phe—OCH3

As described for Example 21, 8.45 g (18.3 mmol) of the title compound were obtained as colorless crystals from 5.6 g (27.6 mmol) of 2-(1,1-dimethyl-ethoxycarbonyl)amino-2-methylpropionic acid and 7.8 g (24.9 mmol) of HCL.H—Pro—Phe—$OCH_3$, after chromatography of the crude product on 250 g of silica gel (ethyl acetate).

TLC: $R_f$(IIIa)=0.87

MS (EI) m/Z=462 (M+H)+

Empirical formula (MW): $C_{24}H_{35}N_3O_6$ (461.56)

EXAMPLE 30

Boc—AiB—Pro—Phe—OH

As described for Example 22, 8.0 g (17.9 mmol) of the title compound were obtained as a pale foam from 8.4 g (18.2 mmol) of the compound from Example 29.

TLC: $R_f$(Ia)=0.6

MS (FAB) m/Z=448 (M+H)+

Empirical formula (MW): $C_{23}H_{33}N_3O_6$ (447.53)

EXAMPLE 31

Nα-{Nδ-[Nα-(1,1-dimethylethoxycarbonyl)-Nα-methyl-π-benzyloxymethyl-(S)-histidyl]-1-[5-(S)-amino-6-cyclohexyl-4-(S)-hydroxy-2-(1-methyl)ethyl]hexanoyl}-(S)-isoleucinyl-2-pyridyl methylamide

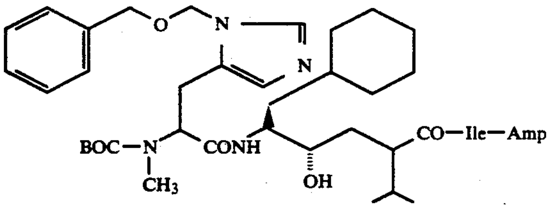

The title compound was obtained following the procedure of example 14, starting with 1.82 g (4.68 mmol) of Boc-Nα-methyl-Nπ-Bom-(S)-histidine and the compound from Example 13.

Yield after chromatography of the crude product on 100 g of silica gel: 3.09 g (3.65 mmol).

TLC (IIIb)=0.62

MW (EI) m/Z=846 (M+H)+

Empirical formula (MW): $C_{47}H_{71}N_7O_7$ (845.53)

EXAMPLE 32

Nα-{Nδ-[Nα-(1,1-dimethylethoxycarbonyl)-Nα-methyl-(S)-histidyl]-1-[5-(S)-amino-6-cyclohexyl-4-(S)-hydroxy-2-(1-methyl)ethyl]-hexanoyl}-(S)-isoleucinyl-2-pyridylmethylamide

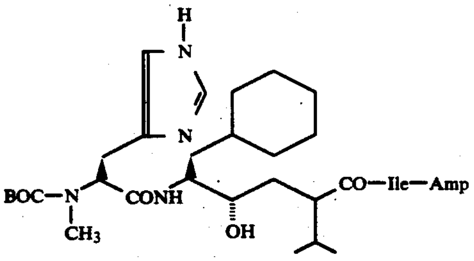

3.0 g (3.55 mmol) of the compound from Example 31 were dissolved in 50 ml of methanol. After addition of 4.53 g (72 mmol) of ammonium formiate, 1.5 g palladium on active carbon and 300 μl (3.1 mmol) triethylamine, the mixture was refluxed for 12 h. After suction filtration the solvent was evaporated and the crude product was extracted from dichloromethane/water. The organic layers were collected, dried over sodium carbonate and evaporated, yielding 2.2 g (3 mmol) of slightly yellow crystals.

TLC: $R_f$(Ia)=0.34

MS (FAB) m/Z=726 (M+H)+

Empirical formula (MW): $C_{39}H_{63}N_7O_6$ (725.45)

EXAMPLE 33

Nα-{Nδ-[Nα-methyl-(S)-histidyl]-1-[5-(S)-amino-6-cyclohexyl-4-(S)-hydroxy-2-(1-methyl)ethyl]hexanoyl}-(S)-isoleucinyl-2-pyridylmethylamide

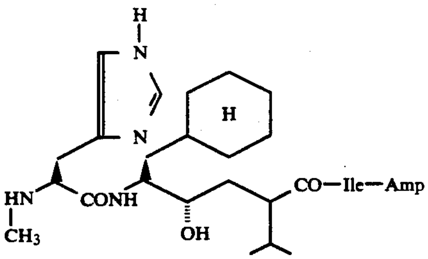

1.8 g (2.48 mmol) of the compound from Example 32 were deprotected and purified according to Example 16, yielding 1.4 g (2.0 mmol) of the title compound.

TLC: $R_f$(IIIb)=0.44

MS (FAB) m/Z=626 (M+H)+

Empirical formula (MW): $C_{34}H_{55}N_7O_4 \times 2HCl$ (698.3)

PREPARATION EXAMPLES (GENERAL FORMULA I)

EXAMPLE I

Nα-{Nδ-{Nα-{1-[2-(1,1-dimethylethoxycarbonyl)amino-2-methyl]propanoyl}-(S)-asparaginyl}-1-[5-(S)-amino-6-cyclohexyl-4-(S)-hydroxy-2-(1-methyl)ethyl]-hexanoyl}-(S)-isoleucinyl-2-pyridylmethylamide

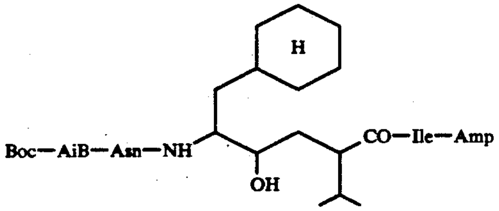

74.5 mg (367 μmol) of 2-(1,1-dimethylethoxycarbonyl)amino-2-methylpropionic acid and 58.35 mg (383 μmol) of 1-hydroxybenzotriazole are dissolved in 5 ml of dimethylformamide and 162 mg (383 μmol) of morpho-CDI are added at −10° C. A solution of 180 mg (306 μmol) of the compound from Example 16 and 46.3 μl of N-methylpiperidine (383 μmol) are dissolved in 5 ml of dimethylformamide. Both solutions are combined, and coupled and worked up as in Example 15. 150 mg of the title compound are obtained.

TLC: $R_f$(IIIb)=0.74

MS (FAB+Li)=780

Empirical formula (MW): $C_{40}H_{67}N_7O_8$ (774.0)

EXAMPLE II

Nα-{Nδ-{Nα-{1-[2-(1,1-dimethylethoxycarbonyl)amino-2-methyl]propanoyl]-(S)-phenylalaninyl}-(S)-asparaginyl}-1(5-(S)-amino-6-cyclohexyl-4-(S)-hydroxy-2-(1-methyl)ethyl]-hexanoyl}-(S)-isoleucinyl-2-pyridylmethylamide

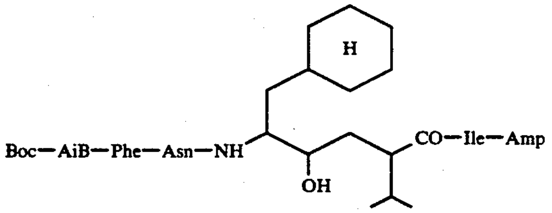

40 mg (192 μmol) of 2-(1,1-dimethylethoxycarbonyl-)amino-2-methylpropionic acid, 31.1 mg (200 μmol) of 1-hydroxybenzotriazole, 120 mg (160 μmol) of the compound from Example 18 and 84.7 mg (200 μmol) of morpho-CDI are reacted in 9 ml of dimethylformamide in accordance with Example 15 to give the title compound. 160 mg are obtained.

TLC: $R_f$(Ic)=0.65

MS (FAB+Li)=927

MS (FAB+Na)=943

Empirical formula (MW): $C_{49}H_{76}N_8O_9$ (921.2)

EXAMPLE III

Nα-{δ-{Nα-{Nα-{Nα-{1-[2-(1,1-dimethylethoxycarbonyl)amino-2-methyl]propanoyl}-(S)-seryl}-(S)-phenylalaninyl}-(S)-asparaginyl}-1-[(5-(S)-amino-6-cyclohexyl-4-(S)-hydroxy-2-(1-methyl)ethyl]hexanoyl}-(S)-isoleucinyl-2-pyidylmethylamide

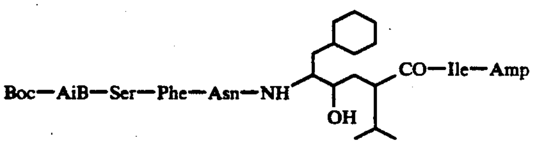

55.7 mg (192 μmol) of Nα-[2-(1,1-dimethylethoxycarbonyl)amino-2-methylpropanoyl]-S-serine, 31.1 mg (200 μmol) 1-hydroxy-benzotriazole, 84.7 mg (200 μmol) of morpho-CDI and 120 mg (100 μmol) of the compound from Example 18 are reacted in 9 ml of dimethylformamide in accordance with Example 15 to give the title compound.

Yield: 150 mg

TLC: $R_f$(Ic)=0.54

MS (RAB)=1008

MS (FAB+Na)=1030

Empirical formula (MW): $C_{52}H_{81}N_9O_{11}$ (1008.3)

EXAMPLE IV

Nα-{Nδ-{1-[2-(1,1-dimethylethoxycarbonyl)amino-2-methyl]propanoyl}-1-[5-(S)-amino-6-cyclohexyl-4-(S)-hydroxy-2-(1-methyl)ethoyl]hexanoyl}-(S)-isoleucinyl-2-pyridylmethylamide

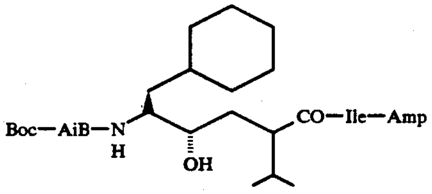

48 mg (0.232 mmol) of DCC were added to a stirred solution, cooled to 0° C., of 43.5 mg (0.214 mmol) of 2-(1,1-dimethylethoxycarbonyl)amino-2-methylpropionic acid and 33.2 mg (0.246 mmol) of HOBT in 1 ml of anhydrous dichloromethane. After about 5 min, a solution of 109.4 mg (0.20 mmol) of the compound from Example 13 and 77 μl (0.70 mmol) of N-methylmorpholine in 1 ml of dichloromethane were added, the cooling bath was removed and the mixture was subsequently stirred at room temperature for 18 h. The precipitated urea was separated off by filtration, and the filtrate was concentrated in vacuo and chromatographed on 15 g of silica gel (ethyl acetate). 67 mg (51%) of the title compound were obtained as colorless crystals; diastereomer mixture.

M.P.: 127°-8° c.

TLC: $R_f$=0.19 (ethyl acetate)

MS (FAB) m/E=660 $(M+H)^+$

Empirical formula (MW): $C_{36}H_{61}N_5O_6$ (659.92)

TABLE 1

The following products were obtained as described for Example IV by reaction of the compound from Example 13 and the appropriate acid (starting compound):

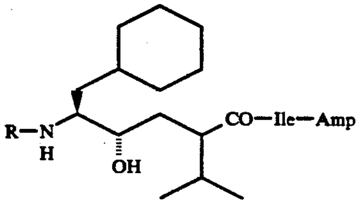

| Ex. No. | R | Yield (%) | MS(FAB) m/e $(M + H)^+$ | $R_f$/eluent (ratio) | Starting compound from Example |
|---|---|---|---|---|---|
| V | Boc—AiB—Val | 48 | 759 | 0.15 (ethyl acetate)[a] | 24 |
| VI a | Boc—AiB—Phe—Val | 28 | 906 | 0.29 (Ia) unpolar[b] | 22 |
| b | Boc—AiB—Phe—Val | 12 | 906 | 0.26 (Ia) polar[b] | |
| VII a | Boc—AiB—Ser—Phe—Val | 12 | 993 | 0.23 (Ia) unpolar | 26 |
| b | Boc—AiB—Ser—Phe—Val | 11 | 993 | 0.19 (Ia) polar | |
| VIII a | Boc—AiB—Ser—Phe | 23 | 912 | 0.20 (Ia) unpolar | 28 |

TABLE 1-continued

The following products were obtained as described for Example IV by reaction of the compound from Example 13 and the appropriate acid (starting compound):

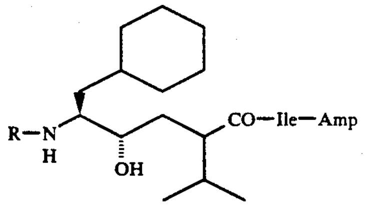

| Ex. No. | R | Yield (%) | MS(FAB) m/e (M + H)+ | $R_f$/eluent (ratio) | Starting compound from Example |
|---|---|---|---|---|---|
| b | Boc—Aib—Ser—Phe | | 912 | 0.17 (Ia) polar | |

[a]Mixture of the $Pr^i$ diastereomers
[b]Pure diastereomers

EXAMPLE IX

Nα-{Nδ-{Nα-{Nα-{1-[2-(1,1-dimethylethoxycarbonyl)amino-2-methyl]propanoyl}-(S)-prolyl}-(S)-phenylalaninyl}-(S)-Nα-methyl-histidyl}-1-[5-(S)-amino-6-cyclohexyl-4-(S)-hydroxy-2-(1-methyl)ethyl]-hexanoyl}-(S)isoleucinyl-2-pyridylmethylamide

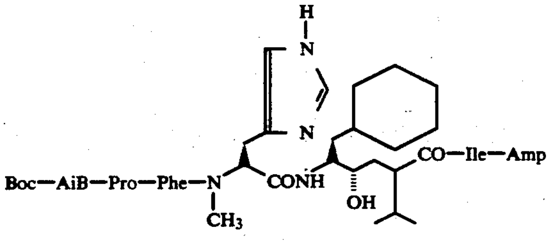

The title compound was obtained as described for Example IV by reaction of the compound from Example 30 (acid) and Example 33 (amino compound).

Yield: 26%

TLC: $R_f$(Ic)=0.78

MS (FAB): 1055

Empirical formula (MW): $C_{57}H_{86}N_{10}P_9$ (1054.65)

EXAMPLE X

Nα-{Nδ-{Nα-{Nα-{Nα-{-1-[2-acetylamino-2-methyl]-propanoyl}-(S)-prolyl}-(S)-phenylalanyl}-(S)-Nα-methyl-histidyl}-1-[5-(S)-amino-6-cyclohexyl-4-(S)-hydroxy-2-(1-methyl)ethyl]hexanoyl}-(S)-isoleucinyl-2-pyridylmethylamide

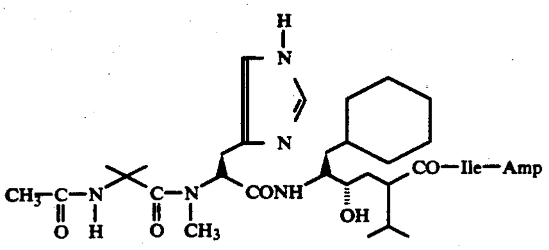

135 mg of 2-acetylamino-2-methylpropionic acid (0.93 mmol) are dissolved in 5 ml of acetonitrile and 1 ml of DMF. The acid is preactivated by 412 mg (0.93 mmol) of BOP. 500 mg/0.62 mmol) of the compound from Example 33 are dissolved in 3 ml acetonitrile, followed by the addition of 75 μl (0.62 mmol) of N-methylpiperidine. After 30′ the two solutions are reunified (put together) and reaction was carried on for 2 h. After evaporation of the solvent the residue was distributed between ethylacetate and sodium hydrogen carbonate. The organic layers was washed successively with sodium hydrogen carbonate and brine, dried over sodium sulfate and evaporated.

Preparative HPLC Dynamax RP-18x, 10% to 90% acetonitrile, yielded 165 mg of a white, fluffy lyophilisate.

HPLC: (Deltapak 7 μ, 100 Å) 10% to 90% acetonitrile in 15′: $R_f$=10.8′

MS (FAB) m/e=753 (M+H)+

Empirical formula (MW): $C_{40}H_{64}N_8O_6$(753.00)

It will be appreciated that the instant specification is set forth by way of illustration and not limitation, and that various modifications and changes may be made without departing from the spirit and scope of the present invention.

What is claimed is:

1. A peptide, wherein

W is Boc or —C(O)$R^3$;

$R^3$ is straight-chain or branched-chain alkyl having up to 8 carbon atoms;

A, B, D, and E are identical or different and represent a direct bond, or a group of having the formula

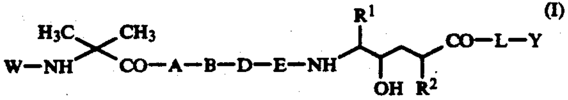

(I)

in which p is O;

$R^4$ is H;

$R^5$ is the side chain of Asn, Phe, Ser, Or Val;

$R^1$ is cyclohexylalkyl; and $R^2$ is lower alkyl;

L is Ile; and

Y is pyridylmethylamino.

2. A peptide according to claim 1, wherein such peptide is Nα-{Nδ{Nα-{Nα{Nα-{1-[2-(1,1-dimethylethoxycarbonyl)amino-2-methyl]propanoyl}-(S)-seryl{-(S)-phenylalanimyl}-(S)-asparaginyl}-1-[(5-(S)-amino-6-cyclohexyl-4-(S)-hydroxy-2-(1-methyl)ethyl]hexanoyl}-(S)-isoleucinyl-2-pyridylmethylamide

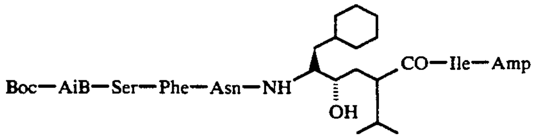

or a physiologically acceptable salt thereof.

3. A peptide according to claim 1, wherein such peptide is Nα-{Nδ-{Nα-{Nα-{1-[2-(1,1-dimethylethoxycarbonyl)amino-2-methyl]propanoyl}-(S)-phenylalaninyl}-(S)-asparaginyl}-1-[5-(S)-amino-6-cyclohexyl-4-(S)-hydroxy-2-(1-methyl)ethyl]hexanoyl}-(S)-isoleucinyl-2-pyridylmethylamide

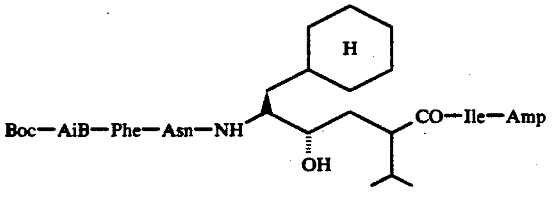

or a physiologically acceptable salt thereof.

4. A peptide according to claim 1, wherein such peptide is Nα-{Nδ-{Nα-{1-[2-(1,1-dimethylethoxycarbonyl)amino-2-methyl]propanoyl}-(S)-valyl-phenylalaninyl}-(S)-asparaginyl}-1-[5-(S)-amino-6-cyclohexyl-4-(S)-hydroxy-2-(1-methyl)ethyl]hexanoyl}-(S)-isoleucinyl-2-pyridylmethylamide of the formula

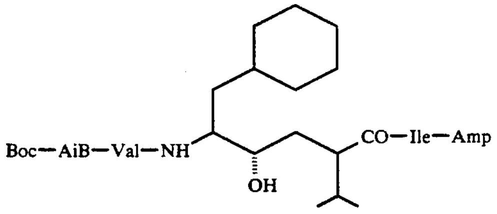

or a physiologically acceptable salt thereof

5. A peptide according to claim 1, wherein such peptide is one of the diastomers of Nα-{Nδ-{Nα-{Nα-{1-[2-(1,1-dimethylethoxycarbonyl)amino-2-methyl]-propanoyl}-(S)-phenylalaninyl}-(S)-valyl}-1-[5-(S)-amino-6-cyclohexyl-4-(S)-hydroxy-2-(1-methyl)ethyl]-hexanoyl}-(S)-isoleucinyl-2-pyridylmethylamide

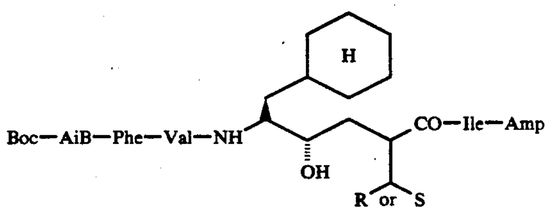

or a physiologically acceptable salt thereof.

6. A peptide according to claim 1, wherein such peptide is one of the diasteromers of Nα-{Nδ-{Nα-{Nα-{1-[2-[1,1-dimethylethoxycarbonyl)amino-2-methyl]-propanoyl}-(S)-seryl}-phenylalaninyl }-(S)-valyl}-1-2-pyridylmethylamide

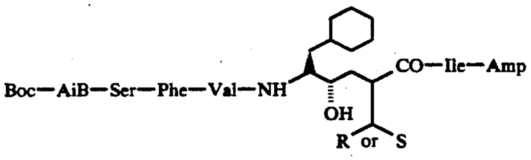

or a physiological acceptable salt thereof.

7. The peptide according to claim 5, wherein the diastereomer is a polar diastereomer.

8. The peptide according to claim 6, wherein the diastereomer is an unpolar diastereomer.

* * * * *

UNITED STATES PATENT AND TRADEMARK OFFICE
CERTIFICATE OF CORRECTION

PATENT NO. : 5,145,951 Page 1 of 2

DATED : September 8, 1992

INVENTOR(S) : Voges et al.

It is certified that error appears in the above-identified patent and that said Letters Patent is hereby corrected as shown below:

Title Page — Delete " [76] Inventors: Klaus-Peter Voges; Dieter Habich; Jutta Hansen; Arnold Paessens, all c/o Bayer Aktiengesellschaft, D 5090 Leverkusen, Bayerwerk, Fed. Rep. of Germany " and substitute -- [75] Inventors: Klaus-Peter Voges; Dieter Habich; Jutta Hansen, all of Wuppertal, Arnold Paessens, Haan, all of Fed. Rep. of Germany --

Title Page — Insert -- [73] Assignee: Bayer Aktiengesellschaft, Leverkusen, Fed. Rep. of Germany --

Col. 30, line 43 — After " peptide " insert -- having the formula

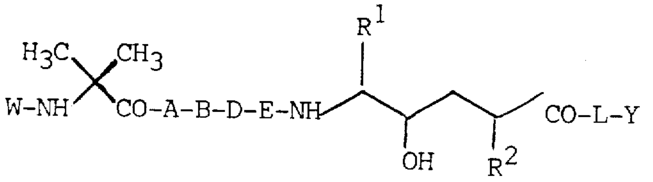

(I) --

Col. 30, lines 48-53 — Delete " having ", delete

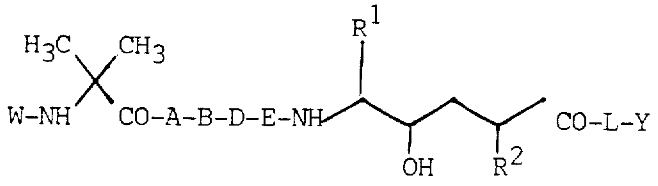

(I) " and substitute -- 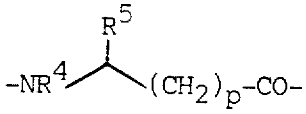 --

UNITED STATES PATENT AND TRADEMARK OFFICE
CERTIFICATE OF CORRECTION

PATENT NO. : 5,145,951

DATED : September 8, 1992
INVENTOR(S) : Voges et al.

It is certified that error appears in the above-identified patent and that said Letters Patent is hereby corrected as shown below:

| | |
|---|---|
| Col. 30, line 65 | Delete " seryl{ " and substitute -- seryl} -- |
| Col. 31, claim 4 line 3 | After " valyl " insert --} -- |
| Col. 31, claim 4 line 4 | Delete " phenylalaninyl} -(S)-asparaginyl} " |
| Col. 32, line 14 | Delete " diastomers " and substitute -- diastereomers -- |
| Col. 32, line 31 | Delete " diasteromers " and substitute -- diastereomers --, after 3rd " {$N_a$- " insert -- {$N_A$- -- |
| Col. 32, line 33 | After " seryl} " insert -- -(S) --; after " valyl} -1- " insert -- [(5-(S)-amino-6-cyclohexyl-4-(S)-hydroxy-2-(1-methyl)ethyl]hexanoyl} -(S)-isoleucinyl- -- |

Signed and Sealed this

Twenty-eighth Day of December, 1993

Attest:

BRUCE LEHMAN

*Attesting Officer*

*Commissioner of Patents and Trademarks*